(12) United States Patent
Rezach et al.

(10) Patent No.: US 7,575,587 B2
(45) Date of Patent: Aug. 18, 2009

(54) TOP-TIGHTENING SIDE-LOCKING SPINAL CONNECTOR ASSEMBLY

(75) Inventors: Alan Rezach, Cordova, TN (US); Mathew M. Morrison, Cordova, TN (US); David L. Brumfield, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 400 days.

(21) Appl. No.: 11/322,824

(22) Filed: Dec. 30, 2005

(65) Prior Publication Data

US 2007/0156142 A1 Jul. 5, 2007

(51) Int. Cl.
*A61B 17/70* (2006.01)

(52) U.S. Cl. .................................................. 606/278

(58) Field of Classification Search ......... 606/250–253, 606/265, 267, 268–270, 277, 278
See application file for complete search history.

(56) References Cited

U.S. PATENT DOCUMENTS

| | | | |
|---|---|---|---|
| 4,569,338 A | 2/1986 | Edwards | |
| 4,827,918 A | 5/1989 | Olerud | |
| 5,047,029 A | 9/1991 | Aebi et al. | |
| 5,053,034 A | 10/1991 | Olerud | |
| 5,254,118 A * | 10/1993 | Mirkovic | 606/264 |
| 5,527,314 A | 6/1996 | Brumfield et al. | |
| 5,534,002 A | 7/1996 | Brumfield et al. | |
| 5,562,662 A | 10/1996 | Brumfield et al. | |
| 5,643,263 A | 7/1997 | Simonson | |
| 5,643,264 A | 7/1997 | Sherman et al. | |
| 5,645,544 A | 7/1997 | Tai et al. | |
| 5,690,630 A | 11/1997 | Errico et al. | |
| 5,741,255 A * | 4/1998 | Krag et al. | 606/264 |
| 5,797,911 A | 8/1998 | Sherman et al. | |
| 5,885,285 A | 3/1999 | Simonson | |
| 5,947,967 A | 9/1999 | Barker | |
| 6,183,473 B1 | 2/2001 | Ashman | |
| 6,210,413 B1 | 4/2001 | Justis et al. | |
| 6,231,575 B1 * | 5/2001 | Krag | 606/264 |
| 6,248,107 B1 | 6/2001 | Foley et al. | |
| 6,520,962 B1 | 2/2003 | Taylor et al. | |
| 6,562,038 B1 | 5/2003 | Morrison | |
| 6,669,697 B1 * | 12/2003 | Pisharodi | 606/264 |
| 6,685,705 B1 | 2/2004 | Taylor | |
| 6,755,830 B2 * | 6/2004 | Minfelde et al. | 606/278 |
| RE39,035 E * | 3/2006 | Finn et al. | 606/264 |
| 2006/0155278 A1 * | 7/2006 | Warnick | 606/61 |
| 2007/0043357 A1 * | 2/2007 | Kirschman | 606/61 |

FOREIGN PATENT DOCUMENTS

WO WO 97/06742 2/1997

* cited by examiner

*Primary Examiner*—Eduardo C Robert
*Assistant Examiner*—Ellen Rust

(57) ABSTRACT

Connector assemblies are provided to couple an elongate member extending along the spinal column to a bone engaging implant engaged to the spinal column. The connector assembly includes a coupler and a clamping member in the coupler that is movable to secure the implant between the clamping member and the coupler when the elongate member is secured in the coupler with an engaging member engaged to the coupler.

18 Claims, 2 Drawing Sheets

TOP-TIGHTENING SIDE-LOCKING SPINAL CONNECTOR ASSEMBLY

BACKGROUND

Spinal implants can be engaged to or along one or more vertebrae of the spinal column for the treatment of various spinal conditions. Fasteners can be provided to secure the implant to a particular location along the spinal column. The implants can be provided to stabilize the spinal column for treatment, either by fixing the spinal column or by permitting at least some motion of the stabilized motion segments.

Multi-axial and uni-axial screws have been employed for securing elongated implants, such as rods or plates, along one or more motion segments of the spinal column. The use of rod to bolt connectors to fix bone screws to spinal rods is another way to secure vertebrae together. Such fasteners can comprise many components or parts that make placement and manipulation of the fastener and the elongated implant cumbersome during surgery to achieve the desired position relative to the spinal anatomy. Fasteners that facilitate securement of the elongated implant in a desired positioning along the spinal column can enhance spinal stabilization procedures.

SUMMARY

According to one aspect, a system for stabilizing a bony segment includes an elongate member positionable along the bony segment and an implant engageable to the bony segment in a transverse orientation to the elongate member. The system also includes a connector assembly for connecting the elongate member to the implant. The connector assembly includes a coupler having a body defining a channel for receiving the elongate member and a clamping member in a passage of the body. The passage extends transversely to the channel. The clamping member includes a portion extending from the body and is configured to receive the implant with the portion of the coupling member. The connector assembly also includes an engaging member movable perpendicularly to the clamping member into contact with the elongate member to contact the elongate member with the clamping member and displace the clamping member and the coupler relative to one another to clamp the implant therebetween.

According to a further aspect, a system for stabilizing a bony segment is provided. The system includes an elongate member positionable along the bony segment and an implant engageable to the bony segment in a transverse orientation to the elongate member. The system also includes a connector assembly for connecting the elongate member to the implant. The connector assembly includes a coupler having a body that defines a channel for receiving the elongate member and a passage in the body that is transversely oriented to the channel. The connector assembly further includes a clamping member in the passage that has a portion projecting from the body to receive the implant. The connector assembly also includes an engaging member threadingly engageable to the coupler in the channel along a first axis, and the clamping member extends along a second axis that is generally orthogonally oriented to the first axis. The channel extends along a third axis that is obliquely oriented to the first axis and to the second axis. When the engaging member is threaded along the first axis in the channel to contact the elongate member, the elongate member moves along the channel and against the clamping member to displace the clamping member in the passage along the second axis to clamp the implant between the clamping member and the coupler.

According to another aspect, a method for coupling an elongate member to an implant engageable to a spinal column includes: providing a coupler having a body defining a channel for receiving the elongate member therein in a first orientation, the body defining a passage extending transversely to the channel for receiving a clamping member therein, the clamping member including a portion projecting from the body to receive the implant in a transverse orientation to the elongate member; advancing an engaging member along the channel in a direction and into contact with the elongate member, wherein the channel is configured to displace the elongate member in the channel along a path obliquely oriented to the clamping member and to the direction along which the engaging member is advanced; and contacting the clamping member with the elongate member to move the clamping member and coupler relative to one another to clamp the implant between the coupler and the clamping member while securing the elongate member against the clamping member.

These and other aspects will be discussed further below.

DETAILED DESCRIPTION OF THE ILLUSTRATED EMBODIMENTS

Figure 1:
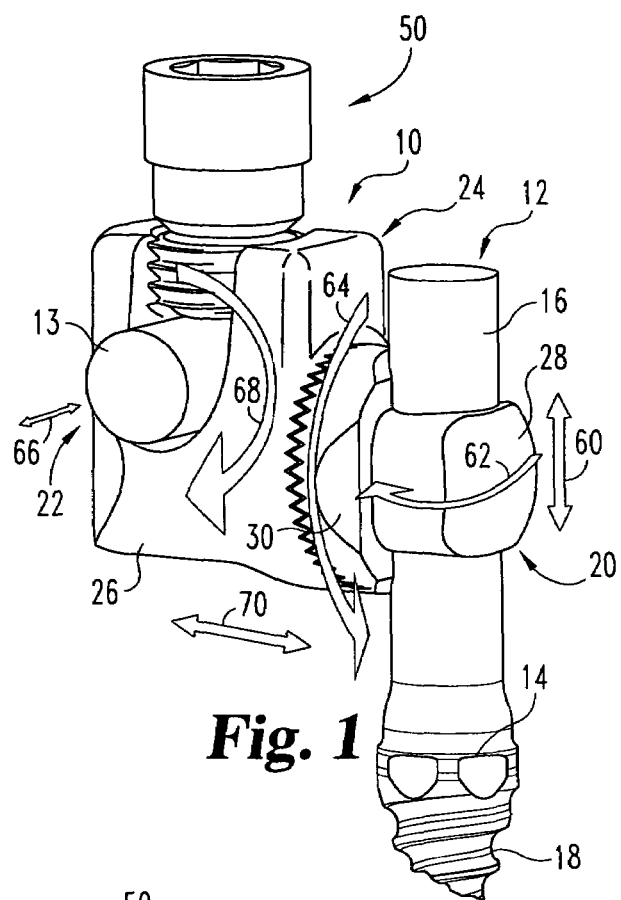
FIG. 1 is a perspective view of a connector assembly and a portion of an implant and elongate member secured to the connector assembly.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Figure 2:
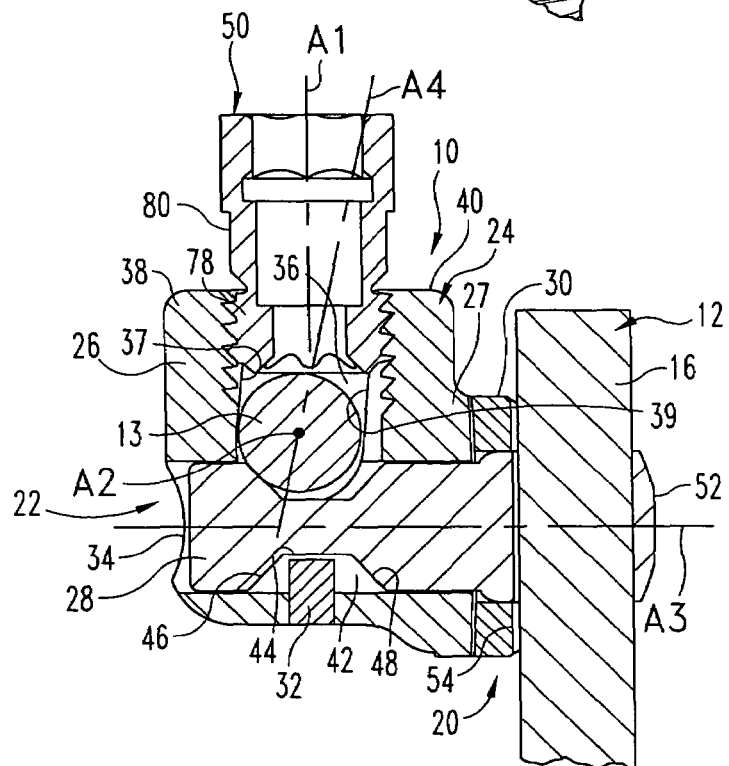
FIG. 2 is a section view of the connector assembly, implant and elongate member of FIG. 1.

FIGS. 1-2 show an embodiment of a connector assembly 10 with an implant 12 and elongate member 13 coupled to connector assembly 10. Connector assembly 10 is operable to connect implant 12, such as a bone anchor, with elongate member 13, such as a spinal rod, to form an implant system. Implant 12 can be a bone screw or other suitable anchoring device engageable to bone or another implant. Implant 12 can include a portion for engagement with connector assembly 10. Elongate member 13 can be a spinal rod or other member positionable along the spinal column to maintain or assist in maintaining one or more vertebrae in a desired position.

Connector assembly 10 can be a top-tightening type connector where the implant and elongate member are coupled to one another simultaneously by securing an engaging member to a coupler extending between the implant and elongate member. The engaging member can secured to the coupler along an axis that is substantially orthogonal to the elongate member, minimizing the lateral exposure required to assemble the assembly.

As used herein, the terms top, bottom, front and back are used to refer various portions of connector assembly 10 and its components. Such terms refer to the orientation of the components as shown in the Figures, and are not intended to limit the orientation of the components relative to the user of the device or its relative positioning in the patient. For example, the top of coupler 24 can be oriented, when implanted, in an anterior, posterior, lateral, medial, oblique or other direction relative to the patient in which the assembly is implanted.

Connector assembly 10 can include an implant coupling portion 20 along one side of a coupler 24 of connector assembly 10. Implant coupling portion 20 can be engaged to a proximal portion 16 of implant 12 In one embodiment, proximal portion 16 can be a post, arm, or other suitable extension or portion for positioning through connector assembly 10. Implant coupling portion 20 can include a first portion of coupler 24 that is movable to clamp implant 12 to connector assembly 10.

Connector assembly 10 can also include an elongate member coupling portion 22 for coupler 24 at a location offset to one side of implant 12. Elongate member 13 can extend through coupler 24 and be engaged thereto with elongate member coupling portion 22 in a transverse orientation to implant 12.

Implant 12 in the illustrated embodiment is a bone screw and can include a distal shaft 18 having a thread profile therealong for engaging bone, and an enlarged head 14 between distal shaft 18 and proximal portion 16. Head 14 can include flats or other tool engaging features to engage a driving tool to facilitate engagement of implant 12 to the underlying bone. Various forms for implant 12 are contemplated, including threaded and non-threaded anchors, uni-planar and multi-axial pivoting arrangements. Bone engaging portions in the form of hooks, clamps, spikes, cables, interbody implants, fusion devices, non-cannulated screws, fenestrated screws, and bolts, are also contemplated, for example. In another form, the implant can be connected to another implant, and/or can be a bone plate, staple, and/or cross-connector extending between spinal rods, for example.

Elongate member 13 can be structured either alone or in combination with one or more other elongate members, implants and/or connector assemblies to provide a desired stabilization effect. In the illustrated embodiment, elongate member 13 is a spinal rod structured to extend between at least two connector assemblies 10 secured to the spinal column with corresponding bone engaging implants. Elongate member 13 can also extend between at least one connector assembly 10 and another implant having any type of suitable connection mechanism to secure elongate member 13 to the implant. Various forms for elongate member 13 are contemplated, including rods, tethers, cables, wires, and plates, for example.

Connector assembly 10 can include coupler 24 having a body 26 for receiving elongate member 13 therethrough in a first direction. Body 26 can also define a passage for receiving a clamping member 28 therein and permitting movement of clamping member 28 relative to body 26 in a second direction that is transversely oriented to the first direction. Clamping member 28 includes a portion projecting from body 26 that is configured to receive at least a portion of implant 12.

Coupler 24 can further include a washer 30 between body 26 and clamping member 28. When proximal portion 16 of implant 13 is secured with coupler 24, implant 16 can be clamped against washer 30 with the washer 30 and implant 12 clamped between implant 12 and body 26. A retaining member 32 can be secured to body 26 and received in a groove of clamping member 28 to axially retain clamping member 28 in body 26 while permitting clamping member 28 to move in body 26 along the axis of clamping member 28. In another embodiment, retaining member 32 can be formed unitarily with body 26 by, for example, upsetting material of body 26, to produce a protrusion that retains clamping member 28.

Body 26 includes a transverse passage 34 for receiving clamping member 28 therein. Transverse passage 34 opens at each side of body 26, although the side opposite of implant 12 could be closed. Body 26 further includes a receiving channel 36 that extends transversely to and is in communication with passage 34. In the embodiment of FIGS. 1 and 2, channel 36 forms a generally U-shape having an open end that opens at a top side of body 26. The U-shape can be defined between a first arm 38 and a second arm 40. First and second arms 38,40 each include an internal thread profile for engaging an engaging member 50. Channel 36 extends between and opens at each of the front and back sides of body 26. Elongate member 13 is positionable in channel 36 such that it projects from the front and back sides of body 26. Channel 36 could also be generally V-shaped or have other suitable configurations.

Clamping member 28 is received in and axially moveable in transverse passage 34 of body 26. Clamping member 28 includes an elongated, pin-like body having an annular groove 42 extending therearound. Groove 42 includes a bottom portion 44 and opposite inclined portions 46,48 extending outwardly from bottom portion 44 to the outer perimeter of clamping member 28. Clamping member 28 further includes a through-bore 54 extending therethrough at an outer end 52 thereof opposite groove 42. Through-bore 54 is sized and shaped to receive proximal portion 16 of implant 12 therethrough. In the illustrated embodiment, through-bore 54 is enclosed by clamping member 28. Other embodiments contemplate through-bore 54 having one or more open sides.

Elongate member 13 is positionable in channel 36, and can be secured therein with engaging member 50 engaged to arms 38,40. As engaging member 50 is threadingly advanced into contact with elongate member 13, elongate member 13 is forced into contact with the adjacent inclined portion 46, 48 of clamping member 28. The camming action of elongate member 13 against, for example, inclined portion 46 as shown, displaces clamping member 28 so that outer end 52 and body 26 are moved toward one another. This in turn pushes implant 12 against washer 30. When washer 30 is firmly seated against body 26, elongate member 13 is locked in position relative to implant 12. Other embodiments contemplate that washer 30 is omitted and the implant is clamped directly against extension portion 27 of body 26 that extends toward implant 12.

In one embodiment, the path along which elongate member 13 moves between arms 38,40 can be obliquely oriented relative to at least one of the path along which engaging member 50 moves into contact with elongate member 13 and the path along which clamping member 28 moves to secure implant 12 to coupler 24. The oblique path along which elongate member 13 is seated in coupler 24 can direct elongate member 13 against the inclined portion 46 of clamping member 28. This in turn axially displaces clamping member 28, and moves implant 12 and body 26 toward one another and clampingly engage washer 30 and implant 12 between clamping member 28 and body 26.

In one embodiment, the thread profile along arms 38,40 extends along an axis A1 that is orthogonal to axis A2 along which elongate member 13 extends. Axis A1 is also orthogonal to the axis A3 along which clamping member 28 and passage 34 extend. The threads provide a path along which engaging member 50 is directed into contact with elongate member 13. Arms 38,40, however, define channel 36 between channel walls 37,39. Walls 37,39 extend along axis A4, which is obliquely oriented to axis A1 and to axis A3. Axis A4 defines the path along which elongate member 13 is moved as it is seated into contact with clamping member 28 by advancement of engaging member 50 along the path defined by axis A1.

Washer 30 extends about clamping member 28 along one side of body 26 adjacent extension portion 27. In one embodiment, washer 30 can include radial splines that interdigitate with a corresponding splined structure on body 26 to secure washer 30 and thus elongate member 13 in position relative to body 26 when clamped thereagainst. Still other embodiments contemplate that washer 30 can be provided in various thickness, tapers, and/or other characteristic to facilitate securement of implant 12 and elongate member 13 in the desired positioning relative to one another.

Connector assembly 10 can provide at least six degrees of adjustability of implant 12 relative to elongate member 13. For example, connector assembly 10 can be axially adjusted along implant 12 in through-bore 54 of clamping member 28, as indicated by arrow 60. The orientation of body 26 and clamping member 28 relative to implant 12 can be adjusted by rotating body 26 and clamping member 28 about implant 12, as indicated by arrow 62. Still further, the positioning of body 26 can be rotationally adjusted about clamping member 28 by rotating body 26 thereabout, as indicated by arrow 64.

Connector assembly 10 can also be axially adjusted along elongate member 13 in channel 36 of body 26, as indicated by arrow 66. The orientation of body 26 and clamping member 28 relative to elongate member 13 can be adjusted by rotating body 26 and clamping member 28 about elongate member 13, as indicated by arrow 68. Still further, the spacing between elongate member 13 and implant 12 can be adjusted along arrow 70 by providing washers of various thicknesses, tapers, or other characteristic, and/or or by increasing an offset distance provided by an extension portion 27 of body 26 that is between channel 36 and the side of the body 26 along which implant 12 extends.

Figure 3:
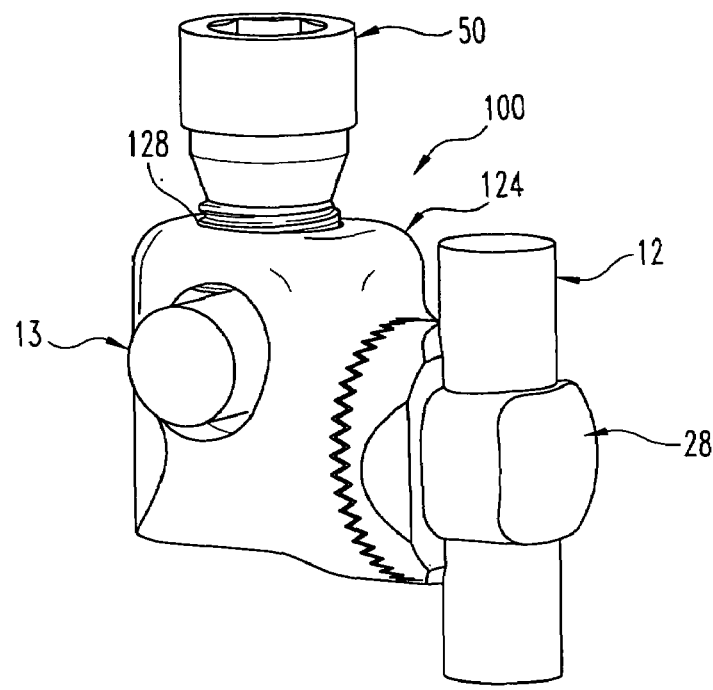
FIG. 3 is a perspective view of another embodiment connector assembly and a portion of an implant and elongate member secured to the connector assembly.
Figure 4:
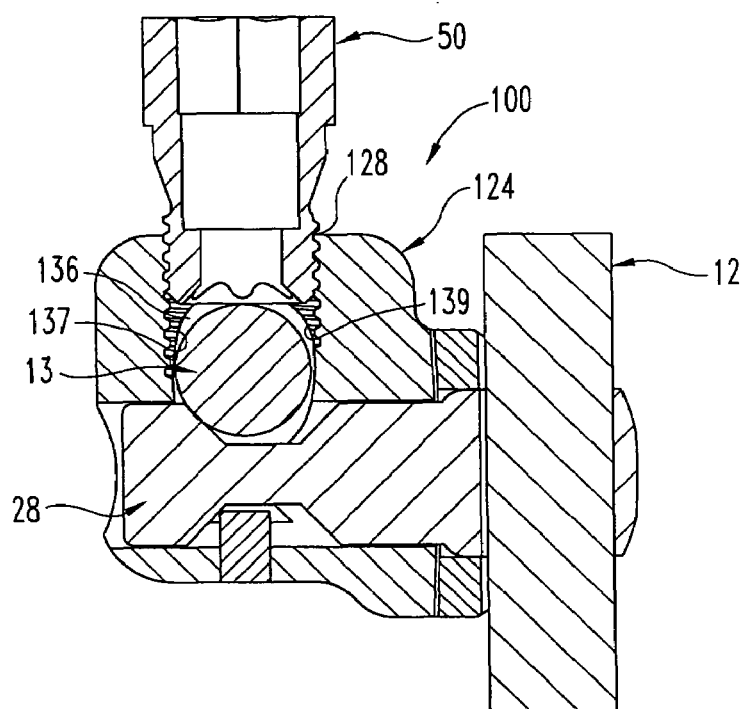
FIG. 4 is a section view of the connector assembly, implant and elongate member of FIG. 3.

FIGS. 3 and 4 show another embodiment connector assembly 100. Connector assembly 100 is substantially identical to connector assembly 10 discussed above. However, connector assembly 100 includes a coupler 124 having a closed channel 136 that is circumscribed by the body of coupler 124. The enclosed channel 136 can receive elongate member 13 by end-loading the elongate member 13 into channel 136. Coupler 124 includes an upper bore 128 in communication with channel 136 to receive an engaging member to secure elongate member 13 therein in contact with clamping member 28. Upper bore 128 can define internal threads to threadingly engage engaging member 50. Like coupler 24, coupler 124 includes channel 136 for receiving and guiding elongate member 13 along a path defined by sidewalls 137, 139 that is obliquely oriented to the axes along which engaging member 50 and clamping 28 are moved.

The arrangement of connector assembly 10,100 allows the positioning of coupler 24,124 relative to implant 12 to be adjusted as needed to accommodate the spinal anatomy. Medial-lateral adjustability can be provided by providing coupler 24 in differing sizes and/or a washer 30 of differing sizes and tapers. Furthermore, the orientation of the portion of the implant extending through through-bore 54 can be varied at various angles.

As also shown in the Figures, engaging member 50 includes a distal threaded portion 78 and a proximal portion 80. Proximal portion 80 can include a recess for receive a driving tool, or can be configured to receive a driving tool thereabout. Proximal portion 80 can be configured to sever or break-off upon application of a threshold torque. Distal portion 78 can include an internal bore that can receive a driving tool to facilitate removal or tightening of distal portion 78 after removal of proximal portion 80.

In use, connector assembly 10,100 can be used in surgical procedures relating to the spine. The surgeon can gain access to a surgical site using any suitable technique, such as through an incision and retraction of tissue, or through minimally invasive access portals or pathways. One or more of the implants 12 can be provided in the form of bone screws that can be threadingly implanted into one or more vertebrae, such as in the pedicle in a posterior stabilization procedure. Proximal portion 16 can extend from the pedicle. If not pre-positioned on proximal portion 16, clamping member 28 can be positioned on implant 12. Furthermore, if not already positioned in coupler 24,124, elongate member 13 can be positioned in the channel thereof.

It is contemplated that assembly of coupler 24,124 with elongate member 13 can be completed prior to implantation of elongate member 13 or during its implantation. In either case, elongate member 13 can be positioned along the spinal column with the coupler secured thereto. The arm of the coupler and the clamping member can be positioned to extend medial-laterally from elongate member 13. The clamping member of the coupler can then be positioned over implant 12 with proximal portion 16 extending through through-bore 54 of the clamping member. Prior to finally securing the coupler to the elongate member and the implant, the orientation of elongate member 13, implant 12, and the coupler can be adjusted relative to one another as discussed above.

Engaging member 50 is positioned to engage the coupler and threaded distally therein to contact elongate member 13. Further advancement of engaging member 50 along the axis defined by the thread profile of the coupler moves elongate member 13 along the obliquely oriented channel of the coupler and into contact with the inclined portion 46 of groove 42 extending about clamping member 28. This in turn moves the coupler and the implant toward one another into clamping engagement. Engaging member 50 can be further advanced until sufficient torque is applied to lock the components of connector assembly 10,100 with implant 12 and elongate member 13.

In spinal surgical procedures, elongate member 13 and one or more connector assemblies 10,100 and other implants discussed herein may be employed unilaterally. Alternatively, a second elongate member 13 and one or more connector assemblies 10,100 and/or other suitable connection mechanism with other implants can be secured to the other side of the vertebral level or levels to be stabilized. Multiple elongate members 13 and corresponding implant/connector assemblies 10,100 can be secured along the same side of the spinal column in either uni-lateral or bi-lateral stabilization procedures.

In one technique, the underlying bone forms a portion of a vertebral body of the spinal column. The underlying bone can be a part of the anterior, oblique, antero-lateral, lateral or posterior vertebral elements, including the pedicle, spinous process, transverse processes, lamina or facet, for example. Applications in techniques along any portion or portions of the spinal column are contemplated, including the cervical, thoracic, lumbar and sacral regions. The connector assemblies, implants and elongate members can be positioned along the spinal column in invasive procedures where skin and tissue are dissected and retracted to expose the implant locations, or in minimally invasive procedures where one or more of the connector assemblies, elongate members and/or implants are guided through at least the tissue or access portals adjacent the column to the desired implantation location.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for stabilizing a bony segment, comprising:
an elongate member positionable along the bony segment;
an implant engageable to the bony segment in a transverse orientation to the elongate member;
a connector assembly for connecting the elongate member to the implant, said connector assembly comprising:
a coupler having a body defining a channel for receiving the elongate member and a clamping member in a passage of said body, said passage extending transversely to said channel, said clamping member including a receiver portion extending from said body and being configured to receive said implant with said receiver portion of said clamping member; and
an engaging member movable generally perpendicularly to said clamping member into contact with said elongate member to contact said elongate member with said clamping member and displace said clamping member and said coupler relative to one another to clamp said implant therebetween wherein said implant is positioned in clamping engagement between said receiver portion of said clamping member and said coupler.

2. The system of claim 1, wherein said engaging member is threadingly engageable to said coupler in said channel.

3. The system of claim 2, wherein said coupler includes threads extending along a first axis for receiving said engaging member along said first axis and said clamping member extends along a second axis generally orthogonal to said first axis, said channel including opposing parallel side walls extending along a third axis obliquely oriented to said first axis and said second axis.

4. The system of claim 3, wherein said channel forms a U-shape that opens on a side of said body to permit said elongate member to be loaded therein through said open side.

5. The system of claim 3, wherein said channel is circumscribed by a body of said coupler and said elongate member is end-loaded into said channel.

6. The system of claim 1, wherein said connector assembly includes a washer between said coupler and said implant.

7. The system of claim 1, wherein said clamping member is an elongated pin having a through-hole adjacent one end of said pin for receiving said implant and an annular groove spaced from said through-hole, said elongate member being received in said annular groove when said implant is clamped between said clamping member and said coupler.

8. The system of claim 7, wherein said annular groove includes a bottom portion and opposite inclined portions extending outwardly from said bottom portion to an outer perimeter of said pin.

9. The system of claim 7, wherein said pin is axially retained in said passage with a retaining pin coupled to said coupler and projecting into said annular groove.

10. The system of claim 1, wherein said connector assembly includes a washer positioned between said coupler and said implant, and wherein said implant is clamped against said washer and said washer is seated against said coupler when said implant is positioned in clamping engagement between said receiver portion of said clamping member and said coupler.

11. A system for stabilizing a bony segment, comprising:
an elongate member positionable along the bony segment;
an implant engageable to the bony segment in a transverse orientation to the elongate member;
a connector assembly for connecting the elongate member to the implant, said connector assembly comprising:
a coupler having a body defining a channel for receiving the elongate member and a passage in said body transversely oriented to said channel, said connector assembly further including a clamping member in said passage that includes a receiver portion projecting from said body to receive said implant;
an engaging member threadingly engageable to said coupler in said channel along a first axis and said clamping member extends along a second axis generally orthogonally oriented to said first axis, wherein said channel includes opposing parallel side walls that each extend along a third axis that is obliquely oriented to said first axis and to said second axis, and when said engaging member is threaded along said first axis in said channel to contact said elongate member, said elongate member moves along said channel and against said clamping member to displace said clamping member in said passage along said second axis to clamp said implant between said clamping member and said coupler wherein said implant is positioned in clamping engagement between said receiver portion of said clamping member and said coupler.

12. The system of claim 11, wherein said channel is circumscribed by a body of said coupler and said elongate member is end-loaded into said channel.

13. The system of claim 11, wherein said connector assembly includes a washer between said coupler and said implant.

14. The system of claim 11, wherein said clamping member includes an elongated pin having a through-hole adjacent one end thereof for receiving said implant therethrough and an annular groove spaced from said through-hole, said elongate member being received in said annular groove when positioned against said clamping member, and wherein said annular groove includes a bottom portion and opposite inclined portions extending outwardly from said bottom portion to an outer perimeter of said pin.

15. The system of claim 11, wherein said elongate member is a spinal rod and said implant is a bone screw with a distal bone engaging portion engageable to a vertebra and a proximal portion received by said clamping member.

16. The system of claim 11, wherein said connector assembly includes a washer positioned between said coupler and said implant, and wherein said implant is clamped against said washer and said washer is seated against said coupler when said implant is positioned in clamping engagement between said receiver portion of said clamping member and said coupler.

17. The system of claim 11, wherein said clamping member is an elongated pin having a through-hole adjacent one end of said pin for receiving said implant and an annular groove spaced from said through-hole, said elongate member being received in said annular groove when said implant is clamped between said clamping member and said coupler.

18. A system for stabilizing a bony segment, comprising:
an elongate member positionable along the bony segment;
an implant engageable to the bony segment in a transverse orientation to the elongate member;
a connector assembly for connecting the elongate member to the implant, said connector assembly comprising:

a coupler having a body defining a channel for receiving the elongate member and a passage in said body transversely oriented to said channel, wherein said channel forms a U-shape that opens along a side of said body and said elongate member can be positioned into said channel through said open side; and said connector assembly further including a clamping member in said passage that includes a portion projecting from said body to receive said implant;

an engaging member threadingly engageable to said coupler in said channel along a first axis and said clamping member extends along a second axis generally orthogonally oriented to said first axis, wherein said channel extends along a third axis that is obliquely oriented to said first axis and to said second axis, and when said engaging member is threaded along said first axis in said channel to contact said elongate member, said elongate member moves along said channel and against said clamping member to displace said clamping member in said passage along said second axis to clamp said implant between said clamping member and said coupler.

* * * * *

UNITED STATES PATENT AND TRADEMARK OFFICE
CERTIFICATE OF CORRECTION

PATENT NO. : 7,575,587 B2
APPLICATION NO. : 11/322824
DATED : August 18, 2009
INVENTOR(S) : Rezach et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 631 days.

Signed and Sealed this

Seventh Day of September, 2010

David J. Kappos
*Director of the United States Patent and Trademark Office*